US010604768B2

(12) United States Patent
Cao et al.

(10) Patent No.: US 10,604,768 B2
(45) Date of Patent: Mar. 31, 2020

(54) SOYBEAN EVENT SHZD32-01 AND METHOD OF USE THEREOF

(71) Applicant: Shanghai Jiao Tong University, Shanghai (CN)

(72) Inventors: Yueping Cao, Shanghai (CN); Peiying Xiao, Shanghai (CN); Luhua Bo, Shanghai (CN); Feng Liu, Shanghai (CN); Yunyun Cui, Shanghai (CN); Linbi Zhou, Shanghai (CN); Jiajin Zhang, Shanghai (CN); Xiangyu Wu, Shanghai (CN); Na Li, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 22 days.

(21) Appl. No.: 15/948,914

(22) Filed: Apr. 9, 2018

(65) Prior Publication Data
US 2018/0230484 A1    Aug. 16, 2018

Related U.S. Application Data

(63) Continuation of application No. PCT/CN2016/101416, filed on Sep. 30, 2016.

(30) Foreign Application Priority Data

Oct. 9, 2015  (CN) .......................... 2015 1 0646846

(51) Int. Cl.
| | | |
|---|---|---|
| C12N 15/82 | (2006.01) | |
| A01H 5/10 | (2018.01) | |
| A01H 1/02 | (2006.01) | |
| A01H 6/54 | (2018.01) | |
| C12Q 1/6895 | (2018.01) | |

(52) U.S. Cl.
CPC .......... *C12N 15/8275* (2013.01); *A01H 1/02* (2013.01); *A01H 5/10* (2013.01); *A01H 6/542* (2018.05); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,535,060 A | 8/1985 | Comai |
| 4,683,195 A | 7/1987 | Mullis et al. |
| 4,683,202 A | 7/1987 | Mullis |
| 5,094,945 A | 3/1992 | Comai |
| 5,463,175 A | 10/1995 | Barry et al. |
| 5,554,798 A | 9/1996 | Lundquist et al. |
| 5,633,435 A | 5/1997 | Barry et al. |
| 6,040,497 A | 3/2000 | Spencer et al. |
| 6,689,880 B2 | 2/2004 | Chen et al. |
| 6,740,488 B2 | 5/2004 | Rangwala et al. |
| 2004/0018518 A1 | 1/2004 | Krieb et al. |

FOREIGN PATENT DOCUMENTS

| | | |
|---|---|---|
| CN | 101252831 A | 8/2008 |
| WO | WO 9200377 A1 | 1/1992 |

OTHER PUBLICATIONS

Lu et al, Scientia Sinica Vitae, 2014, vol. 44, No. 4, pp. 406-415 (Year: 2014).*
Toki, Seiichi et al., "Expression of a maize ubiquitin gene promoter-bar chimeric gene in transgenic rice plants," Plant Physiol. 100, pp. 1503-1507 (1992).
Block M.De, Etal., "Engineering herbicide resistance in plants by expression of a detoxifying enzyme," EMBO Journal, vol. 6, No. 9, pp. 2513-2518 (1987).
Hearing, Janet Etal., "Addition of truncated oligosaccharides to influenza virus hemagglutinin results in its temperature-conditional cell-surface expression," Journal of Cell Biology, vol. 108, pp. 355-365 (Feb. 1989).
Voytas, Daniel F. Etal., "copia-like retrotransposons are ubiquitous among plants," Proc. Natl. Acad. Sci. USA, vol. 89, pp. 7124-128, Genetics (Aug. 1992).
Holland, Michael J. Etal., "In vitro transcription of PCT templates," PCT Protocols: A guide to Methods and Applications, Academic Press, Inc., pp. 169-176 (1990).
Haymes et al., "Nucleic acid hybridisation—A practical Approach," pp. 245, IRL Press, Oxford, ISBN 0-947946-23-3 (1985).
Diwan, Noa, et al., "Simple sequence report DNA markers in alfalfa and perennial and annual Medicago species," Genome, 40: 887-895 (1997).
Cheng, Suzanne Etal., "Template integrity is essential for PCT amplification of 20- to 30-kb sequences from genomic DNA," Technical Tips, PCR Methods and Applications, published by Cold Spring Harbor Laboratory Press, 4:294-298, ISSN 1054-9803/95 (1994).

* cited by examiner

*Primary Examiner* — Eileen B O Hara
(74) *Attorney, Agent, or Firm* — Mei & Mark LLP; Manni Li (57) ABSTRACT

Soybean plant and seed comprising soybean transgenic event SHZD32-01 and DNA molecules unique to the event. Also provided are use of the plant parts, seeds; the soybean transgenic event SHZD32-01 comprises at least one of the nucleic acid molecules of SEQ ID NO: 1, SEQ ID NO: 2, SEQ ID NO: 3, SEQ ID NO: 4, SEQ ID NO: 9, and their complete complementary sequences. The method of use include the method for producing soybean with tolerance to herbicide glyphosate, producing a soybean-based commercial product, and controlling weeds in a field comprising soybean plants. Soybean strains comprising the soybean event SHZD32-01 exhibits strong tolerance to glyphosate and is helpful for weeds control. DNA detection of the soybean event SHZD32-01 is useful for identifying the soybean event SHZD32-01 in a sample and may be applied to methods for breeding soybean plants comprising the DNA.

20 Claims, 1 Drawing Sheet
Specification includes a Sequence Listing.

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Recombinant DNA molecule

<400> SEQUENCE: 1 tgcatttaa cgaattaatt                                                  20

<210> SEQ ID NO 2
<211> LENGTH: 20
<212> TYPE: DNA
<213> ORGANISM: Artificial Sequence
<220> FEATURE:
<223> OTHER INFORMATION: Recombinant DNA molecule

<400> SEQUENCE: 2
gtttcccgcc ataagggtgt                                                 20

<210> SEQ ID NO 3
<211> LENGTH: 1054
<212> TYPE: DNA
<213> ORGANISM: Artificial Sequence
<220> FEATURE:
<223> OTHER INFORMATION: Recombinant DNA molecule

<400> SEQUENCE: 3
tgccatcatc aatggtcaca cggagtggga ctacagaatt tgaaaatagt agagaaaaca     60
gcagtgggca cttgctattt tcctttcatc attggaaatt aaatggggaa agggaaaaaa    120
```

| | |
|---|---|
| atatttctgt ttctacaat gaatgacaat aataggagat ttggttttcg tagaatcaga | 180 |
| attattcaaa aaaagaaaaa cagaattcca ttgaacgaat tccctgcact tttgttgata | 240 |
| ctaagggtat atctctctct tgatattggg agattatttc ctccatagag tacaattttt | 300 |
| tttttttttt acttttttca agtttcaaca agttttaca gtaaatacat agaaatttaa | 360 |
| ttatttcaa aattggataa aacgccttca tttatagaga attttctctc tccctgtgta | 420 |
| tttatttctt ataacttgaa gcttctttgg aatgctgctt tatcttttaa aacagcttgt | 480 |
| tttaaggtta acattaacta aattccctat catctactta ctttgccggc cgactagtta | 540 |
| taaaagaatt agatgattca ttgcctcaac ctattagggt tttcccgatg aaggattaaa | 600 |
| ttagacataa ttaggtgcat gaaggcttaa gtttgatctt ccttattatt attgtattaa | 660 |
| aaaaaaagca aattcacta actctctatg tttaatactt gttacactca aagtcactca | 720 |
| ttattggaac cctacacatc cccttccccc ttcgctgttg caactcattg cacaaagacc | 780 |
| ccctaaccgt ctatttcatt aactttagga tgttgctaag cacatgcatt ttaacgaatt | 840 |
| aattcggggg atctggattt tagtactgga ttttggtttt aggaattaga aattttattg | 900 |
| atagaagtat tttacaaata caaatacata ctaagggttt cttatatgct caacacatga | 960 |
| gcgaaaccct ataggaaccc taattccctt atctgggaac tactcacaca ttattatgga | 1020 |
| gaaactcgag ctcctatagg cggtagcctc agcg | 1054 |

<210> SEQ ID NO 4
<211> LENGTH: 820
<212> TYPE: DNA
<213> ORGANISM: Artificial Sequence
<220> FEATURE:
<223> OTHER INFORMATION: Recombinant DNA molecule

<400> SEQUENCE: 4

| | |
|---|---|
| gaagaggccc gcaccgatcg cccttcccaa cagttgcgca gcctgaatgg cgaatgctag | 60 |
| agcagcttga gcttggatca gattgtcgtt tcccgccata agggtgtata ctatagttag | 120 |
| ttgtatatgg ctagtactat ggcggcggtt ccgaccacca cgagaccgta gtacaacatg | 180 |
| ggcatgctgt tgctcttggt tgatggagag gaggtggag gaggggatga gatggtgaag | 240 |
| gggcttagaa catcacccat gatggttata atttagtgtt ttggtgaaat tcgaagagag | 300 |
| aacacaagtt ttgaagaaag ttcttttgta gacaactaac tatagtatac acccttatgg | 360 |
| ccttatctat tcaatgaggg ttataattta gatgatggaa ttattggagg gggtttattg | 420 |
| atttattttt attgaaaata ttaaattaat gttaagtagt taagctaaaa gccgtggtgg | 480 |
| ttatgttatc attgaagggg agaatataat tatttttgc tcaagttgga tataatatgt | 540 |
| catggaatat ttactatttt agagaagact aagaggagca gacaaagaaa tgtactataa | 600 |
| agggggcagt gaacaaagat gggtgagagt gaccagaatt ttgtagataa gtgtcctgtg | 660 |
| tcccttgcac gttctatttc tttctttgcc tggggttttg ggaagcccct atggttaaat | 720 |
| gctaaaaaac aattttttgt atctattcgg aaatcaaatt tgcttctatt catcacaggt | 780 |
| aaagagacat gtgatttact aagatgtcat tcataaatcc | 820 |

<210> SEQ ID NO 5
<211> LENGTH: 22
<212> TYPE: DNA
<213> ORGANISM: Glycine max

<400> SEQUENCE: 5

| | |
|---|---|
| tgccatcatc aatggtcaca cg | 22 |

<210> SEQ ID NO 6
<211> LENGTH: 25
<212> TYPE: DNA
<213> ORGANISM: Deinococcus radiodurans

<400> SEQUENCE: 6
cgctgaggct accgcctata ggagc                                          25

<210> SEQ ID NO 7
<211> LENGTH: 25
<212> TYPE: DNA
<213> ORGANISM: Escherichia coli

<400> SEQUENCE: 7
gaagaggccc gcaccgatcg ccctt                                          25

<210> SEQ ID NO 8
<211> LENGTH: 22
<212> TYPE: DNA
<213> ORGANISM: Glycine max

<400> SEQUENCE: 8
ggatttatga atgacatctt ag                                             22

<210> SEQ ID NO 9
<211> LENGTH: 4727
<212> TYPE: DNA
<213> ORGANISM: Artificial Sequence
<220> FEATURE:
<223> OTHER INFORMATION: Recombinant DNA molecule

<400> SEQUENCE: 9
tgccatcatc aatggtcaca cggagtggga ctacagaatt tgaaaatagt agagaaaaca    60
gcagtgggca cttgctattt tcctttcatc attggaaatt aaatgggaa agggaaaaaa   120 atatttctgt tttctacaat gaatgacaat aataggagat ttggttttcg tagaatcaga   180
attattcaaa aaaagaaaaa cagaattcca ttgaacgaat tccctgcact tttgttgata   240
ctaagggtat atctctctct tgatattggg agattatttc ctccatagag tacaattttt   300 ttttttttt acttttttca gtttcaaca agttttaca gtaaatacat agaaatttaa     360
ttattttcaa aattggataa aacgccttca tttatagaga attttctctc tccctgtgta   420
tttatttctt ataacttgaa gcttctttgg aatgctgctt tatcttttaa aacagcttgt   480
tttaaggtta acattaacta aattccctat catctactta ctttgccggc cgactagtta   540
taaaagaatt agatgattca ttgcctcaac ctattagggt tttcccgatg aaggattaaa   600
ttagacataa ttaggtgcat gaaggcttaa gtttgatctt ccttattatt attgtattaa   660
aaaaaaagca aattacacta actctctatg tttaatactt gttacactca agtcactca   720 ttattggaac cctacacatc cccttcccc ttcgctgttg caactcattg cacaaagacc    780
ccctaaccgt ctatttcatt aactttagga tgttgctaag cacatgcatt taacgaatt    840 aattcggggg atctggattt tagtactgga ttttggtttt aggaattaga aatttttattg   900 atagaagtat tttacaaata caaatacata ctaagggttt cttatatgct caacacatga   960
gcgaaaccct ataggaaccc taattccctt atctgggaac tactcacaca ttattatgga  1020
gaaactcgag ctcctatagg cggtagcctc agcgtattcg aatctagcac caagagcttc  1080
aaggtgagcg aagaactgag ggtaggactt tctgatgtgg tgtgcaccgg tgattctaag  1140

-continued

```
tggagcatct gctctgagac caagaagggt gagaagcatg atcattctgt ggtcaccgtg      1200
accatcagcg gtgataccac cagcaaggtg agcagaacca gtaacggaga gagaatcggc      1260
ggtctctctt gctctaagac caagtctttc aagctcagct ctggtgtcag agattctatc      1320
gcattccttg agtctaagag tagcaacgtt ttcccaggtg gtatcaccct cagcgaaggc      1380
agcagcagcg gtaagagctt gcacggcgtc ggtgaaggaa tcaccatctc tagtaacagc      1440
gtggagaggt ctaccacctc tcacggtaag ggtatcacct tctctaacga tatcagcacc      1500
catctctcta agaacgttca cagcttcctt ctcaccctgg aggtcgtgtt ctctaaggtt      1560
agaaagtcta acctcacctg ggagaagagc agcggcggta aggatagcag cggaaccagg      1620
gtaatcacca ggaacgagca ctctacctgg tctgtacttc tgaccaccag ggatggagat      1680
tcttctaagg tcatcggagg cagtagctct aacaccgaaa tcagagaggg tgtcaagtgt      1740
ctgtctaaga ggagcgtggg acttgatatc accggtgagt ctaagttcga gtccgtcagg      1800
aagaagagga ccgaggaaca taagggcgga agcgtactgg gaggatcttt cggcggaaac      1860
ctccactgta ccacctctaa ctggaccgga aacgagata gggagtctac catcgttgga      1920
ggacacccaa gcaccaagtc tttcgagggc ttcaagaagg tcaccctgag gtctcttacc      1980
aagggaatca gggtaatcgg taacgaaagt tgtaccagag tgagagcag caacacccat      2040 aaggagtctg gccaccgcag cagcgttacc tgggttaagg gtaacaccag cctgtggtct      2100
agcaccgaaa cctctgatca cggcgtcatc accaacaagc tcaacaccag caccccaatc      2160
tctgaggcat ctgagcatag cttcggcatc ctcagaggta ccacaccaa caactctggt      2220 ttcaccctca gcgagagcag cggcgaggag gtatctagtg gtgtagttct tggatggctg      2280
tgctctaagt tcacctctga gttctctagc tggatgcacg ataacgtcga aggtagctgg      2340
aagagcgtcg gatcccttct ccgccgtgga aacagaagac atgaccttaa gaggacgaag      2400
ctcagagcca attaaagtca tcccactctt cttcaatccc caagatgaag aaattggata      2460
agctcgtgga tgctgctgag tcttcagaga accgataag ggagatttcc tttgactgga      2520
tttagagaga ttggagataa gagatggggtt ctgcacacca ttgcagattc tgctaacttg      2580
agccatggct atcgttcgta aatggtgaaa attttcagaa aattgctttt gctttaaaag      2640
aaatgattta aattgctgca atagaagtag aatgcttgat tgcttgagat tcgtttgttt      2700
tgtatatgtt gtgttgactc gagagagata gatttgtaga gagagactgg tgatttcagc      2760
gtgtcctctc caaatgaaat gaacttcctt atatagagga aggtcttgcg aaggatagtg      2820
ggattgtgcg tcatccctta cgtcagtgga gatatcacat caatccactt gctttgaaga      2880
cgtggttgga acgtcttctt tttccacgat gctcctcgtg ggtgggggtc catctttggg      2940
accactgtcg gcagaggcat cttgaacgat agcctttcct ttatcgcaat gatggcattt      3000
gtaggtgcca ccttcctttt ctactgtcct tttgatgaag tgacagatag ctgggcaatg      3060
gaatccgagg aggtttcccg atattaccct ttgttgaaaa gtctcaatag ccctttggtc      3120
ttctgagact gtatctttga tattcttgga gtagacgaga gtgtcgtgct ccaccatgtt      3180
atcacatcaa tccacttgct ttgaagacgt ggttggaacg tcttcttttt ccacgatgct      3240
cctcgtgggt ggggtccat ctttgggacc actgtcggca gaggcatctt gaacgatagc      3300 cttttccttta tcgcaatgat ggcatttgta ggtgccacct tccttttcta ctgtcctttt      3360
gatgaagtga cagatagctg gcaatggaa tccgaggagg tttccgata ttaccctttg      3420 ttgaaaagtc tcaatagccc tttggtcttc tgagactgta tctttgatat tcttggagta      3480
gacgagagtg tcgtgctcca ccatgttggc aagctgctct agccaatacg caaaccgcct      3540
```

-continued

```
ctccccgcgc gttggccgat tcattaatgc agctggcacg acaggtttcc cgactggaaa    3600
gcgggcagtg agcgcaacgc aattaatgtg agttagctca ctcattaggc accccaggct    3660
ttacacttta tgcttccggc tcgtatgttg tgtggaattg tgagcggata caatttcac     3720 acaggaaaca gctatgacca tgattacgaa ttcgagctcg gtacccgggg atcctctaga    3780
gtcgacctgc aggcatgcaa gcttggcact ggccgtcgtt ttacaacgtc gtgactggga    3840
aaaccctggc gttacccaac ttaatcgcct tgcagcacat ccccctttcg ccagctggcg    3900
taatagcgaa gaggcccgca ccgatcgccc ttcccaacag ttgcgcagcc tgaatggcga    3960
atgctagagc agcttgagct tggatcagat tgtcgtttcc cgccataagg gtgtatacta    4020
tagttagttg tatatggcta gtactatggc ggcggttccg accaccacga gaccgtagta    4080
caacatgggc atgctgttgc tcttggttga tggagaggag ggtggaggag gggatgagat    4140
ggtgaagggg cttagaacat cacccatgat ggttataatt tagtgttttg gtgaaattcg    4200
aagagagaac acaagttttg aagaaagttc ttttgtagac aactaactat agtatacacc    4260
cttatggcct tatctattca atgagggtta taatttagat gatggaatta ttggaggggg    4320
tttattgatt tattttattt gaaaatatta aattaatgtt aagtagttaa gctaaaagcc    4380
gtggtggtta tgttatcatt gaaggggaga atataattat ttttgctca agttggatat     4440 aatatgtcat ggaatattta ctattttaga gaagactaag aggagcagac aaagaaatgt    4500
actataaagg gggcagtgaa caaagatggg tgagagtgac cagaattttg tagataagtg    4560
tcctgtgtcc cttgcacgtt ctatttcttt ctttgcctgg ggttttggga agccccctatg   4620 gttaaatgct aaaaacaat tttttgtatc tattcggaaa tcaaatttgc ttctattcat     4680
cacaggtaaa gagacatgtg atttactaag atgtcattca taaatcc                  4727
```

```
<210> SEQ ID NO 10
<211> LENGTH: 20
<212> TYPE: DNA
<213> ORGANISM: Artificial Sequence
<220> FEATURE:
<223> OTHER INFORMATION: Primer and/or probe

<400> SEQUENCE: 10
ctttgccggc cgactagtta                                                   20

<210> SEQ ID NO 11
<211> LENGTH: 21
<212> TYPE: DNA
<213> ORGANISM: Artificial Sequence
<220> FEATURE:
<223> OTHER INFORMATION: Primer and/or probe

<400> SEQUENCE: 11
actaaaatcc agatcccccg a                                                 21

<210> SEQ ID NO 12
<211> LENGTH: 20
<212> TYPE: DNA
<213> ORGANISM: Artificial Sequence
<220> FEATURE:
<223> OTHER INFORMATION: Probe

<400> SEQUENCE: 12
agcttggatc agattgtcgt                                                   20

<210> SEQ ID NO 13
```

```
<211> LENGTH: 20
<212> TYPE: DNA
<213> ORGANISM: Artificial Sequence
<220> FEATURE:
<223> OTHER INFORMATION: Probe

<400> SEQUENCE: 13
tgggtgatgt tctaagcccc                                                  20

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tgttgctaag cacatgcatt tta                                              23

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
acaccagagc tgagcttgaa                                                  20

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
tgcccatgtt gtactacggt c                                                21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gtcgtgactg ggaaaaccct                                                  20

<210> SEQ ID NO 18
<211> LENGTH: 20
<212> TYPE: DNA
<213> ORGANISM: Artificial Sequence
<220> FEATURE:
<223> OTHER INFORMATION: Primer and/or probe

<400> SEQUENCE: 18
ttaactttag gatgttgcta                                                  20

<210> SEQ ID NO 19
<211> LENGTH: 19
<212> TYPE: DNA
<213> ORGANISM: Artificial Sequence
<220> FEATURE:
<223> OTHER INFORMATION: Primer and/or probe

<400> SEQUENCE: 19
```

```
acccttagta tgtatttgt                                                   19
```

```
<210> SEQ ID NO 20
<211> LENGTH: 24
<212> TYPE: DNA
<213> ORGANISM: Artificial Sequence
<220> FEATURE:
<223> OTHER INFORMATION: Primer and/or probe

<400> SEQUENCE: 20 tggatttttag tactggattt tggt                                            24
```

```
<210> SEQ ID NO 21
<211> LENGTH: 834
<212> TYPE: DNA
<213> ORGANISM: Glycine max

<400> SEQUENCE: 21
tgccatcatc aatggtcaca cggagtggga ctacagaatt tgaaaatagt agagaaaaca      60
gcagtgggca cttgctattt tcctttcatc attggaaatt aaatgggaa agggaaaaaa     120
atatttctgt tttctacaat gaatgacaat aataggagat ttggttttcg tagaatcaga    180
attattcaaa aaagaaaaa cagaattcca ttgaacgaat tccctgcact tttgttgata     240
ctaagggtat atctctctct tgatattggg agattatttc ctccatagag tacaattttt    300
tttttttttt acttttttca gtttcaaca agttttttaca gtaaatacat agaaatttaa    360
ttattttcaa aattggataa aacgccttca tttatagaga attttctctc tccctgtgta    420
tttatttctt ataacttgaa gcttctttgg aatgctgctt tatcttttaa aacagcttgt    480
tttaaggtta acattaacta aattcccctat catctactta ctttgccggc cgactagtta   540
taaaagaatt agatgattca ttgcctcaac ctattagggt ttttcccgatg aaggattaaa   600
ttagacataa ttaggtgcat gaaggcttaa gtttgatctt ccttattatt attgtattaa    660
aaaaaaagca aattacacta actctctatg tttaatactt gttacactca aagtcactca    720
ttattggaac cctacacatc cccttcccccc ttcgctgttg caactcattg cacaaagacc   780
ccctaaccgt ctatttcatt aactttagga tgttgctaag cacatgcatt ttaa          834
```

```
<210> SEQ ID NO 22
<211> LENGTH: 723
<212> TYPE: DNA
<213> ORGANISM: Glycine max

<400> SEQUENCE: 22
ataagggtgt atactatagt tagttgtata tggctagtac tatggcggcg gttccgacca     60
ccacgagacc gtagtacaac atgggcatgc tgttgctctt ggttgatgga gaggagggtg    120
gaggagggga tgagatggtg aaggggctta gaacatcacc catgatggtt ataatttagt    180
gttttggtga aattcgaaga gagaacacaa gttttgaaga agttcttttt gtagacaact    240
aactatagta tacacccctta tggccttatc tattcaatga gggttataat ttagatgatg   300
gaattattgg aggggggttta ttgatttatt tttattgaaa atattaaatt aatgttaagt   360
agttaagcta aaagccgtgg tggttatgtt atcattgaag gggagaatat aattattttt    420
tgctcaagtt ggatataata tgtcatggaa tatttactat tttagagaag actaagagga    480
gcagacaaag aaatgtacta taaaggggc agtgaacaaa gatgggtgag agtgaccaga     540
attttgtaga taagtgtcct gtgtcccttg cacgttctat ttctttcttt gcctggggtt    600
```

-continued

```
ttgggaagcc cctatggtta aatgctaaaa aacaattttt tgtatctatt cggaaatcaa        660
atttgcttct attcatcaca ggtaaagaga catgtgattt actaagatgt cattcataaa        720
tcc                                                                     723
```

US 10,604,768 B2

SOYBEAN EVENT SHZD32-01 AND METHOD OF USE THEREOF

CROSS-REFERENCE TO RELATED APPLICATIONS

The subject application is a continuation of PCT/CN2016/101416 filed on Sep. 30, 2016, which claims priority on Chinese Patent Application No. 201510646846.7 filed on Oct. 9, 2015 in China. Both PCT international application and Chinese priority application are incorporated herein by reference.

FIELD OF THE INVENTION

The present invention relates to a new soybean transgenic event SHZD32-01. The event exhibits relatively strong tolerance to herbicide glyphosate. The present invention also relates to methods for using the soybean plant parts, plant seeds, and its products related to the transgenic event SHZD32-01.

BACKGROUND OF THE INVENTION

Soybean (*Glycine max*) is an important economic crop. Herbicide (especially glyphosate) tolerance is one of the critical traits for desirable soybean. Glyphosate, a kind of herbicide that has activity on broad spectra of plant species, is the major ingredient of Roundup® (Monsanto Colo., St. Louis, Mo.), a safe herbicide with short half-life in environment. When applied to the surfaces of the plants, glyphosate moves systemically through the entire plants. Glyphosate is phytotoxic because of its inhibition of the shikimic acid pathway, which provides a precursor for the synthesis of aromatic amino acids. Glyphosate inhibits the enolpyruvyl-3-phoshoshikimate synthase (EPSPS) found in plants.

Glyphosate tolerance may be obtained by expressinG mutants that have lower affinity for glyphosate and retain metabolic activity in the presence of glyphosate (U.S. Pat. Nos. 5,633,435; 5,094,945; 4,535,060 and 6,040,497). Glyphosate degrading enzymes in plant tissues (U.S. Pat. No. 5,463,175) are also capable of conferring glyphosate tolerance to cells. These genes are used for producing transgenic crops with tolerance to glyphosate, and consequently, glyphosate may be used for effective weed control with minimal damage to crops. Glyphosate tolerance has already been genetically engineered into corn (U.S. Pat. No. 5,554,798), wheat (U.S. Pat. No. 6,689,880), cotton (U.S. Pat. No. 6,740,488), soybean (WO 9200377), and canola (US Patent Appl. 20040018518) so far. The transgenes for glyphosate tolerance and the transgenes for other herbicides tolerance, e.g., the bar gene, (Toki el al., 1992; Thompson et al., 1987, for glufosinate herbicide tolerance) are also useful as selectable markers or scorable markers and may provide useful phenotypes for selection of plants in connection with other agronomically useful traits.

The expression of foreign genes in plants is influenced by their positions along chromosomes. Great differences are observed in transformants due to the different insertion sites of foreign genes. As a result, a large number of events need to be screened to identify the event characterized by the optimal expression of the introduced foreign gene. It has been observed in different transgenic events that there is a wide range of variation in the expression level of the introduced gene in different tissues. There are also different temporal and spatial expression patterns, such as the differences in the relative expression of a transgene in various plant tissues. Therefore, hundreds to thousands of different events need to be produced and screened for a single event that has the desired transgene expression levels and patterns for commercial purpose. An event with desired levels or patterns of transgene expression is helpful for introgressing the transgene into other genetic backgrounds through traditional methods of sexual crossing. The progeny thus obtained may maintain the transgene expression characteristics of the original transformant. The strategy ensures reliable expression in a number of varieties which are well adapted to local growing conditions.

The detection of the presence of a particular event may be accomplished by identifying whether a progeny of a sexual cross comprises the transgene of interest. Besides, the method for detecting a particular event is necessary to comply with regulations and requirements for the pre-market approval and labeling of foods derived from genetically modified crops. It is possible to detect the presence of a transgene by any nucleic acid examination method such as the polymerase chain reaction (PCR) or DNA hybridization using polynucleic acid probes. These detection methods are generally concerned with frequently used genetic elements, such as promoters, terminators, marker genes, etc., therefore, these methods are not valid for discriminating between different events, particularly those produced using the same DNA vector unless the chromosomal DNA sequence (flanking DNA) adjacent to the inserted transgene is known. For example, Windels et al. use a pair of primers spanning the junction between the inserted transgene and flanking DNA to identify herbicide tolerant soybean event 40-3-2 in 1999, one primer specifically includes the sequence of the inserted transgene and the other primer includes the sequence of the flanking DNA (U.S. Pat. Nos. 6,893,826; 6,825,400; 6,740,488; 6,733,974 and 6,689,880; 6,900,014 and 6,818,807).

SUMMARY OF THE INVENTION

The present invention provides soybean transgenic event SHZD32-01 and methods of use thereof, said soybean transgenic plant SHZD32-01 is derived from soybean cultivars that exhibit tolerance to glyphosate herbicide. The present invention also provides usage of the soybean plant parts, seeds, and their products from the event SHZD32-01.

The present invention provides transgenic soybean plants event with glyphosate tolerance, newly designated as SHZD32-01, including plant parts, seeds comprising the event, and products derived from the plants, plant parts and products.

The present invention provides a novel DNA molecule comprised in the soybean cell genome related to the event SHZD32-01, as well as various methods used for identifying the novel DNA molecule in samples.

The present invention further provides a recombinant DNA molecule present in the soybean event SHZD32-01 and comprises at least one of the nucleic acid molecules having sequence shown in SEQ ID NO: 1, SEQ ID NO: 2, SEQ ID NO: 3, SEQ ID NO: 4, SEQ ID NO: 9 and their complete complementary sequences.

The present invention provides a recombinant DNA molecule comprising nucleotide sequence SEQ ID NO:2.

The present invention provides a recombinant DNA molecule comprising nucleotide sequence SEQ ID NO:3.

The present invention provides a recombinant DNA molecule comprising nucleotide sequence SEQ ID NO:4.

The present invention provides a recombinant DNA molecule comprising nucleotide sequence SEQ ID NO:9.

The present invention provides a recombinant DNA molecule comprising nucleotide sequences SEQ ID NO:1 and SEQ ID NO: 2.

The present invention provides a recombinant DNA molecule comprising nucleotide sequences SEQ ID NO:3 and SEQ ID NO: 4.

The recombinant DNA molecule of the present invention is from the soybean event SHZD320-01. Soybean event SHZD320-01 have representative seeds deposited with China Center for Type Culture Collection (CCTCC), the Accession number for the deposit is CCTCC NO: P201513, the address of the CCTCC is Wuhan university, Luojiashan, Wuchang, Wuhan, 430072, China; the date of deposit is Aug. 18, 2015; and the description and classification of the deposited biological material is soybean cultivated soybean species, soybean SHZD32-01 *Glycine max* (L) Merr., and the deposited material is representative seeds for the soybean event SHZD320-01.

The recombinant DNA molecule of the present invention is provided and present in soybean plants, soybean plant cells, soybean seeds, soybean plant parts, or in commercial products.

The present invention further provides DNA primers or probes, comprising sufficiently long contiguous nucleotide sequences from SEQ ID NO:9 and its complementary sequence, the primers or probes are used for diagnosing transgenic event SHZD32-01. Such probes and primers specifically hybridize to SEQ ID NO:1-4 or SEQ ID NO:9 under high stringency hybridization conditions, but do not hybridize to a target molecule without the sequences from either SEQ ID NO:1-4 or SEQ ID NO:9 under high stringency hybridization conditions.

The present invention provides a pair of DNA molecules comprising a first DNA molecule and a second DNA molecule that differs from the first DNA molecule. Both DNA molecules comprise a sufficiently long contiguous nucleotide sequence from SEQ ID NO:9, or its complementary sequence, and together, work as DNA primers with the DNA of the transgenic event SHZD32-01 for diagnosing soybean transgenic event SHZD32-01 via PCR amplification reaction.

The present invention also provides a method for detecting the presence of DNA corresponding specifically to the soybean event SHZD32-01 DNA molecule in samples. Such method comprises the following steps: (a) contacting a sample comprising a DNA with the DNA probe according to claim 11; (b) subjecting the sample and the DNA probe to stringent hybridization conditions; and (c) detecting hybridization of the DNA probe to the sample, and if the DNA probe hybridizes to the DNA molecule, then the DNA corresponding specifically to the soybean event SHZD32-01 DNA is present in the sample.

The present invention provides a method for detecting the presence of DNA corresponding specifically to the soybean event SHZD32-01 DNA in samples. The method comprises the following steps: (a) contacting a sample comprising a DNA with the DNA primer pair according to claim 12; (b) performing a nucleic acid amplification reaction and producing the amplicon, which comprises one of the nucleic acid sequences given in SEQ ID 1-4 and SEQ ID NO: 9 and their complete complementary sequences; and (c) detecting the amplicon of the above reaction, and if there is amplicon in the reaction, then the DNA corresponding specifically to the soybean event SHZD32-01 DNA is present in the sample.

The present invention provides a DNA detection kit comprising a pair of DNA primers or at least a DNA probe, where (a) the pair of DNA primers comprise at least a DNA molecule which comprises a nucleic acid sequence that is long enough contiguous from SEQ ID: 9 or its complete complementary sequence, and the pair of DNA primers may also produce amplified fragment of soybean event SHZD32-01; (b) at least one DNA probe is used for detecting the soybean event SHZD32-01.

The present invention provides soybean plants comprising SHZD32-01, and planting a field with the soybean plants comprising event SHZD32-01 and treating the field with glyphosate to control weed growth therein.

The technical solution of the present invention is:

A soybean plant or part thereof comprising soybean event SHZD32-01, wherein representative soybean seed comprising event SHZD32-01 have been deposited under CCTCC accession number P201513.

A seed of the soybean plant comprising soybean event SHZD32-01, wherein the seed comprises the soybean transgenic event SHZD32-01.

A soybean commercial product produced from the seed, wherein the commodity product comprises the soybean transgenic event SHZD32-01.

The soybean commercial product is defined as food, flour, soybean meal, or oil.

The soybean plant part is further defined as cell, pollen, ovule, flower, shoot, root, or leaf.

The soybean plant is further defined as a progeny plant of any generation of the soybean plant comprising the soybean transgenic event SHZD32-01, wherein the progeny plant comprises the soybean transgenic event SHZD32-01.

The soybean plant or part thereof is capable of producing an event SHZD32-01 diagnostic amplicon.

The diagnostic amplicon comprises SEQ ID NO: 1 or SEQ ID NO: 2.

A seed comprising the soybean transgenic event SHZD32-01, wherein the seed is capable of producing a diagnostic amplicon for the event SHZD32-01.

The diagnostic amplicon for the event SHZD32-01 that comprises SEQ ID NO: 1 or SEQ ID NO: 2.

The food, flour, soybean meal, or oil is further defined as comprising a nucleic acid that produces a diagnostic amplicon for the event SHZD32-01 when tested in a DNA amplification method, and the diagnostic amplicon comprises SEQ ID NO: 1 or SEQ ID NO: 2.

A method for producing a soybean plant tolerant to glyphosate comprising introducing into the genome of the plant the soybean transgenic event SHZD32-01.

The method for producing a soybean plant tolerant to glyphosate comprising the following steps: (a) crossing a first soybean plant comprising event SHZD32-01 with a second soybean plant lacking event SHZD32-01 to produce progeny plants; and (b) selecting at least one progeny of the first plant comprising the soybean transgenic event SHZD32-01 and being tolerant to glyphosate.

The method for producing a soybean plant tolerant to glyphosate, further comprising selfing the progenies of the first plant comprising the soybean transgenic event SHZD32-01 and being tolerant to glyphosate to produce second generation progeny plants, and selecting at least a homozygous progeny of the first plant comprising the soybean transgenic event SHZD32-01.

A glyphosate tolerant soybean plant, seed, or DNA comprising part thereof comprising a glyphosate resistant protein G10-EPSPS and capable of producing a diagnostic amplicon for the event.

The glyphosate tolerant soybean plant, seed, or DNA comprising part thereof, characterized in that the amplicon diagnostic for event SHZD32-01 comprises SEQ ID NO: 1 or SEQ ID NO: 2.

A method of producing a soybean commodity product, characterized in that, it comprises (a) obtaining the soybean plant or part thereof of claim 1, and (b) producing a soybean commodity product from the soybean plant or part thereof.

The commodity product is defined as food, flour, flakes, protein isolate, or oil.

A method for planting soybean plants in a field with controlled weeds, characterized in that, soybean plants comprising event SHZD32-01 are used, and the method comprises treating the field with an amount of glyphosate effective to control the growth of weeds, wherein the soybean plants exhibit tolerance to glyphosate.

The method for controlling the weeds in a field comprising soybean plants comprising event SHZD32-01, wherein treating the field is carried out from V1 to R4 stage of growth.

The present invention provides soybean plants designated transgenic event named SHZD32-01, which exhibits strong tolerance to herbicide glyphosate. The representative soybean seeds thereof have been deposited under CCTCC accession number CCTCC NO: P201513. The present invention also provides a novel DNA molecule related to the event SHZD32-01 and methods of use thereof. The present invention also provides soybean seeds, progenies, plant parts, and commercial products from event SHZD32-01. The present invention also provides methods of using the event SHZD32-01 and producing soybean with tolerance to glyphosate.

The present invention provides recombinant DNA molecules related to the soybean transgenic event SHZD32-01. These recombinant DNA molecules may comprise nucleotide molecules having a nucleotide sequence representing a region of the genomic DNA flanking the transgene insertion, and/or a region of the transgene insertion, and/or a contiguous sequence of any of these regions such as a region of the junction between the transgene insertion and flanking genomic DNA of soybean event SHZD32-01. The present invention also provides DNA molecules useful as diagnostic primers and probes for the soybean transgenic event SHZD32-01 and diagnostic amplicons for the presence of the soybean event SHZD32-01. Soybean plants, plant cells, plant parts, commodity products, progeny, and seeds comprising these molecules are also disclosed.

The present invention provides methods, compositions, and kits for detecting the presence and/or absence of the DNA derived from the soybean event SHZD32-01 in samples. The present invention provides a method for detecting SHZD32-01 by contacting a sample comprising a DNA with a primer set that, when used in a nucleic acid amplification reaction with genomic DNA from soybean event SHZD32-01, produces an amplified DNA diagnostic for soybean event SHZD32-01, performing a nucleic acid amplification reaction thereby producing the amplified DNA, and detecting the presence and/or absence of the amplified DNA. The present invention also provides a method for detecting SHZD32-01 by contacting a sample comprising DNA with a probe that, when used in a hybridization reaction with DNA from soybean event SHZD32-01, hybridizes to a DNA molecule specific for soybean event SHZD32-01, performing a hybridization reaction, and detecting the hybridization of the probe to the DNA molecule. Kits comprising the methods and compositions of the present invention useful for detecting the presence of DNA derived from the soybean event SHZD32-01 are also provided.

The present invention provides a soybean plant, seed, plant cell, progeny plant, plant part, or commodity product derived from a plant, plant cell, or seed of the soybean transgenic event SHZD32-01. The present invention also provides a soybean plant, seed, plant cell, plant part, or commodity product comprising a recombinant DNA molecule having a nucleotide sequence selected from the group consisting of SEQ ID NO: 1-4 and SEQ ID NO: 9, and complements and fragments thereof.

The present invention also provides a soybean plant, seed, plant cell, progeny plant, plant part, or commodity product derived from the plant or seed of the soybean transgenic event SHZD32-01 and comprising a recombinant DNA molecule that produces an amplified DNA molecule comprising SEQ ID NO: 1 and/or SEQ ID NO: 2 in the DNA amplification reaction.

The present invention in another aspect provides a method to control weeds in a field of soybean plants comprising SHZD32-01, wherein the method comprises planting a field with soybean seed comprising the event SHZD32-01, the representative seed has been deposited as CCTCC accession No. P201513, allowing the seed to germinate and treating the plants with an effective dose of glyphosate to control weed growth in the field.

According to another aspect of the present invention, a method for producing a soybean plant that tolerates an application of glyphosate is provided, which comprises the steps of: (a) sexually crossing a first parental glyphosate tolerant soybean plant comprising the event SHZD32-01 and a second parental soybean plant that lacks the glyphosate tolerance, thereby producing a plurality of progeny plants; and (b) selecting a progeny plant that tolerates application of glyphosate. Details may be described as: the methods to produce plant or seed with tolerance to glyphosate by sexual hybridization include sexually crossing a first glyphosate tolerant soybean plant comprising the event SHZD32-01 with a second soybean plant to produce seeds, growing the seeds to produce a second generation of progeny plants, treating the second generation of progeny plants with glyphosate, and selecting a second generation progeny plant that is tolerant to glyphosate. The methods may also include selfing the selected progeny plant to produce a plurality of second generation progeny plants and selecting from these second generation progeny plants a glyphosate tolerant plant. The methods may also include sexually crossing the selected progeny plant with another soybean plant to produce seed, growing the seed to produce a second generation of progeny plants, treating the second generation of the progeny plants with glyphosate, and selecting a second generation progeny plant that is tolerant to glyphosate. The present invention provides methods of producing a soybean plant and/or seed that tolerates application of glyphosate herbicide by selfing a glyphosate tolerant soybean event SHZD32-01 plant, thereby producing seed, growing the seed to produce progeny plants, treating the progeny plants with glyphosate; and selecting a progeny plant that is tolerant to glyphosate. The methods may also include sexually crossing a first parental glyphosate tolerant soybean plant comprising event SHZD32-01 and a second glyphosate tolerant parental soybean plant, screening a progeny that is tolerant to glyphosate with DNA molecular markers genetically linked with glyphosate resistant phenotype found in every parent.

One aspect of the present invention provides plants or seeds from the soybean transgenic event SHZD32-01, or compositions and methods for detecting the presence of a DNA transgene/genomic junction region from a soybean event SHZD32-01 plant or seed or products derived from plant parts or seed. DNA molecules are provided that comprise at least one transgene/genomic junction DNA molecule selected from the group consisting of SEQ ID NO: 1 and SEQ ID NO:2, and complements thereof, wherein the junction molecule spans the insertion site that comprises a heterologous DNA inserted into the genome of the soybean cell and the genomic DNA from the soybean cell flanking the insertion site. Such junction sequences may, in one aspect of the present invention, be defined as comprising nucleotide 824-844 or 3994-4014 of SEQ ID NO:9, respectively. In other aspects of the present invention, the junctions may be defined as including additional portions of the flanking genome and transgene, for example, and may be defined as comprising one or more sequence as given by nucleotides 804-844, 774-844, 824-864, 824-894, 774-894, 3974-4014, 3944-4014, 3994-4034, 3996-4014, 3996-4066, or 3946-4066 of SEQ ID NO: 9. Such sequences and plants and seeds comprising these sequences therefore form one aspect of the present invention.

The present invention provides a novel DNA molecule that comprises a DNA transgene/genomic region SEQ ID NO: 3 or the complement thereof, from the soybean transgenic event SHZD32-01. A soybean plant and seed comprising SEQ ID NO:3 in its genome is an aspect of the present invention. SEQ ID NO:3 further comprises SEQ ID NO: 1 in its entirety.

According to another aspect of the present invention, a DNA molecule is provided that comprises a DNA transgene/genomic region SEQ ID NO: 4, or the complement thereof, wherein the DNA molecule is novel in the soybean event SHZD32-01. A soybean plant and seed comprising SEQ ID NO: 4 in its genome is an aspect of the present invention. SEQ ID NO: 4 further comprises SEQ ID NO:2 in its entity.

Any nucleotide primer pair derived from SEQ ID NO:3 or SEQ ID NO:4, or SEQ ID NO:9 or the complements thereof, that, when used in a DNA amplification reaction, produces a diagnostic amplicon for the soybean event SHZD32-01-derived tissue, such as an amplicon that comprises SEQ ID NO: 1 or SEQ ID NO:2 or any portion of SEQ ID NO:9, respectively, is another embodiment of the present invention. In one particular embodiment, the primer pair may consist of primer A (SEQ ID NO:5) and primer D (SEQ ID NO:8).

Another aspect of the present invention is a soybean plant, seed, or product derived from a plant or seed comprising the event SHZD32-01, in which the genomic DNA, when isolated from the soybean plant, or seed, or product, produces an amplicon in a DNA amplification method that comprises SEQ ID NO: 1 or SEQ ID NO:2.

Another aspect of the present invention is a soybean plant, seed, or product derived from a plant or seed comprising SHZD32-01, in which the genomic DNA, when isolated from the soybean plant, seed, or product, produces an amplicon in a DNA amplification method, wherein DNA primer molecules SEQ ID NO: 5 or SEQ ID NO:6 are used in the DNA amplification method.

Still another aspect of the present invention is a soybean plant, seed, product, or commodity derived from the plant or seed, comprising the soybean transgenic event SHZD32-01, in which the genomic DNA, when isolated from the soybean plant, seed, or product, produces an amplicon in a DNA amplification method, wherein DNA primer molecules SEQ ID NO: 7 and SEQ ID NO:8 are used in the DNA amplification method. The product or commodity may comprise, without limitation, a food or feed product comprising or derived from one or more of the following products of a soybean plant comprising the event SHZD32-01: lecithin, fatty acids, glycerol, sterol, edible oil, defatted soybean meal, soyfoods including defatted and toasted soy meals, soy milk curd, tofu, soy flour, textured soy protein, and soy protein fiber.

According to another aspect of the present invention, a method for detecting the presence of a DNA corresponding specifically the soybean transgenic event SHZD32-01 DNA in a sample is provided. Such method comprises: (a) contact a sample comprising a DNA with a DNA primer; (b) performing a nucleic acid amplification reaction, thereby producing the amplicon; and (c) detecting the amplicon, wherein said amplicon comprises SEQ ID NO:1 or SEQ ID NO:2. A kit comprising DNA primer molecules that, when used in a DNA amplification method, produces an amplicon comprising SEQ ID NO: 1 or SEQ ID NO: 2 is a further aspect of the present invention.

According to another aspect of the present invention, a method for detecting the presence of a DNA corresponding specifically to the soybean event SHZD32-01 in a sample is provided. The method comprises: (a) contacting a sample comprising a DNA with a probe that hybridizes under stringent hybridization conditions with genomic DNA from the soybean event SHZD32-01 and does not hybridize under the stringent hybridization conditions with a control soybean plant DNA; (b) subjecting the sample and probe to stringent hybridization conditions; and (c) detecting hybridization of the probe to the soybean event SHZD32-01 DNA, wherein the probe comprises SEQ ID NO: 1 or SEQ ID NO:2. The sample may comprise a progeny seed, plant, or plant part comprising the soybean event SHZD32-01, or any of the following products derived from a plant comprising SHZD32-01: lecithin, fatty acids, glycerol, sterol, edible oil, defatted soybean meal, soyfoods including defatted and toasted soy meals, soy milk curd, tofu, soy flour, soy protein concentrate, isolated soy protein, hydrolyzed vegetable protein, textured soy protein, and soy protein fiber. A kit comprising a DNA probe comprising a DNA molecule that is homologous or complementary to SEQ ID NO: 1 or SEQ ID NO:2 is an aspect of the present invention. A kit comprising a DNA molecule comprising SEQ ID NO: 18, SEQ ID NO: 19, or SEQ ID NO:20, or their complement sequences, is also an aspect of the present invention.

DETAILED DESCRIPTION

The present invention relates to a novel soybean transgenic event SHZD32-01 that provides glyphosate tolerance, and the plant parts and seed and products produced from plants, plant parts, seed, and products comprising the event. The present invention provides DNA molecules that are novel in the genome of soybean cells comprising SHZD32-01. The presences of the DNA molecules in a sample may be detected by various methods. The present invention provides a method to control weeds in a field of plants comprising SHZD32-01 by treating the weeds in the field comprising plants comprising event SHZD32-01 with a glyphosate herbicide.

The following definitions and methods are provided to better define the present invention. Terms are to be understood according to conventional usage by those of ordinary skill in the relevant art.

As used herein, the term "soybean" means *Glycine max* and includes all bred plant varieties or soybean material.

As used herein, the term "comprising" means "including but not limited to".

"Glyphosate" refers to N-phosphonomethylglycine and its salts, glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation comprising glyphosate. Examples of commercial formulations of glyphosate include, without restriction, those sold by Monsanto Company as ROUNDUP®, ROUNDUP® ULTRA, ROUNDUP®ULTRAMAX, ROUNDUP®CT, ROUNDUP®EXTRA, ROUNDUP®BIACTIVE, ROUNDUP®BIOFORCE, RODEO®, POLARIS®, SPARK® and ACCORD® herbicides, all of which comprise glyphosate as its isopropylammonium salt; ROUNDUP®WEATHERMAX (glyphosate potassium salt), those sold by Monsanto Company as ROUNDUP®DRY and RIVAL® herbicides, which comprise glyphosate as its ammonium salt; that sold by Monsanto Company as ROUNDUP®GEOFORCE, which comprises glyphosate as its sodium salt; and that sold by Syngenta Crop Protection as TOUCHDOWN® herbicide, which comprises glyphosate as its trimethylsulfonium salt. Herbicides also include herbicides comprising the above ingredients produced by various domestic pesticide manufacturers. Treatment of a field comprising glyphosate tolerant soybean plants comprising the event SHZD32-01 with any of these glyphosate herbicide formulations controls weed growth in the field and does not affect the growth or yield of the soybean plants comprising SHZD32-01.

A transgenic "event" is a body obtained from a plant produced by transgenic of plant cells with heterologous DNA, for example, a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA and a parental line that does not comprise the inserted DNA.

"Recombinant DNA molecule" refers to a DNA molecule that would not normally be found in nature and is made with human intervention. A "recombinant DNA molecule" is artificially synthesized from two DNA molecules heterologous to each other and comprises a polynucleotide sequence. In the present invention, the foreign gene is incorporated into the soybean genome and bound with the soybean genome of the insertion site to form a recombinant DNA molecule.

A glyphosate tolerant soybean may be bred by first sexually crossing a first parental soybean plant consisting of a soybean plant grown from a transgenic glyphosate tolerant soybean plant comprising SHZD32-01 or an soybean plant that is a progeny of the cross of such a plant that expresses the glyphosate tolerant phenotype, and a second parental soybean plant that lacks the tolerance to glyphosate, thereby producing a plurality of hybrid first progeny plants; and then selecting the progeny plant with tolerance to glyphosate by treatment of glyphosate herbicide. These steps may further include the back-crossing of the glyphosate tolerant progeny plant to the second parental soybean plant or a third parental soybean plant, then selecting progeny by application with glyphosate or by identification with molecular markers associated with the trait thereby producing a soybean plant that tolerates the application of glyphosate herbicide. Molecular markers may be used that comprise the junction DNA molecules identified at the 5' and 3' sites of insertion of the transgene in the event SHZD32-01.

Method of breeding in the present invention includes that two different transgenic plants are mated to produce offspring that comprise two independently segregating, exogenous transgenes, and back-crossing to a parental plant, out-crossing with a non-transgenic plant as previously described, vegetative propagation, and conventional breeding methods that are commonly used for different traits and crops found in the existing literature.

A "probe" is an isolated nucleic acid which is attached to a conventional detectable label or reporter molecule, for example, a radioactive isotope, a ligand, a chemiluminescent agent, or an enzyme. Such a probe is complementary to a strand of a target nucleic acid, in the case of the present invention, to a strand of genomic DNA from a soybean plant comprising the transgenic event SHZD32-01 whether from a soybean plant or seed or from a sample or extract of the plant or seed that includes DNA from the event.

Probes according to the present invention include not only deoxyribonucleic or ribonucleic acids, but also polyamides and other probe materials that bind specifically to a target DNA sequence and may be used to detect the presence of that target DNA sequence.

"Primers" are isolated polynucleic acids that are annealed to a complementary target polynucleic acid strand by nucleic acid hybridization to form a hybrid between the primer and the target polynucleic acid strand, then extended along the target polynucleic acid strand by a polymerase.

Primer pairs of the present invention refer to their use for the amplification of a target polynucleic acid molecule by the polymerase chain reaction (PCR) or other conventional nucleic acid amplification methods.

Probes and primers are generally 11 polynucleotides or more in length, preferably 18 polynucleotides or more, more preferably 24 polynucleotides or 30 polynucleotides or more. Such probes and primers hybridize specifically to a target nucleotide molecule under high stringency hybridization conditions. Preferably, probes and primers according to the present invention have complete sequence identity with the target molecule, though probes differ from the target sequence, probes retain the ability to hybridize to target sequences under high stringency conditions as designed by conventional methods.

Methods for preparing and using probes and primers are described, for example, in Sambrook et al. (1989); Ausubel et al. (1992); and Innis et al. (1990). PCR-primer pairs (a primer set) may be derived from a known sequence, for example, by using computer programs intended for that purpose such as Primer (Version 0.5, ©1991, Whitehead Institute for Biomedical Research, Cambridge, Mass.).

Primers and probes based on the flanking genomic DNA and insert sequences disclosed in the present invention (SEQ ID NOS: 1-4 and 9) may be used to confirm and correct the disclosed sequences by conventional methods, for example, by isolating the corresponding DNA molecule from the seed comprising SHZD32-01, and confirming the nucleic acid sequence of such molecules. Additional associated DNA molecules may be isolated from the genome of a cell comprising SHZD32-01 that comprise the transgene insert, genomic flanking regions, and fragments of these molecules and used as primers or probes.

The nucleic acid probes and primers of the present invention hybridize under stringent conditions to a target DNA sequence. Any conventional nucleic acid hybridization or amplification method may be used to identify the presence of DNA from the SHZD32-01 event in a sample. Nucleic acid molecules or fragments thereof are capable of specifically hybridizing to other nucleic acid molecules under certain circumstances. Two nucleic acid molecules are capable of specifically hybridizing to one another if the two molecules are capable of forming an anti-parallel, double-stranded nucleic acid structure and are of sufficient length to maintain this structure under high stringency conditions. A nucleic acid molecule is said to be the "complement" of another nucleic acid molecule if they exhibit complete complementarity. Molecules are said to exhibit "complete complementarity" when every nucleotide of one of the molecules is complementary to a nucleotide of the other. Two molecules are said to be "minimally complementary" if they may hybridize to one another with sufficient stability to permit them to remain annealed to one another under at least conventional "low-stringency" conditions. Similarly, the molecules are said to be "complementary" if they may hybridize to one another with sufficient stability to permit them to remain annealed to one another under conventional "high-stringency" conditions. Conventional stringency conditions are described by Sambrook et al., 1989, and by Haymes et al. (1985). Departures from complete complementarity are therefore permissible, as long as such departures do not completely preclude the capacity of the molecules to form a double-stranded structure. In order for a nucleic acid molecule to serve as a primer, it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0×sodium chloride/sodium citrate (SSC) at about 45° C., followed by a wash of 2.0×SSC at 50° C., are known to those skilled in the art or may be found in Current Protocols in Molecular Biology, John Wiley & Sons, N.Y. (1989), 6.3.1-6.3.6. For example, the salt concentration in the wash step may be selected from a low stringency of about 2.0×SSC at 50° C. to a high stringency of about 0.2×SSC at 50° C. In addition, the temperature in the wash step may be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NOS:1-4, and 9 complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NOS:1-4, and 9 complements thereof or fragments of either under high stringency conditions. In one aspect of the present invention, a preferred marker nucleic acid molecule of the present invention comprises the nucleic acid sequence as set forth in SEQ ID NO: 1 or SEQ ID NO:2 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 1 or SEQ ID NO:2 or complements thereof or fragments of either. marker DNA molecules that comprise SEQ ID NO:1, or SEQ ID NO:2, or complements thereof or fragments of either may be used as markers in plant breeding methods to identify the progeny of genetic crosses similar to the methods described for simple sequence repeat DNA marker analysis, in Cregan et al. (1997); all of which is herein incorporated by reference in the entirely. The hybridization of the probe to the target DNA molecule may be detected by any number of methods known to those skilled in the art, these may include, but are not limited to, fluorescent tags, radioactive tags, antibody based tags, and chemiluminescent tags.

Regarding the amplification of a target nucleic acid sequence (for example, by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence and is part of a nucleic acid template. For example, to determine whether the soybean plant resulting from a sexual cross comprises the transgenic event SHZD32-01 or whether a soybean sample collected from a field comprises the transgenic event SHZD32-01, or a soybean extract, such as a meal, flour or oil, comprises the transgenic event SHZD32-01. DNA extracted from a soybean plant tissue sample or extract may be subjected to a nucleic acid amplification method using a primer pair that includes a primer derived from the genomic region adjacent to the insertion site of inserted heterologous transgene DNA, and a second primer derived from the inserted heterologous transgene DNA to produce an amplicon that is diagnostic for the presence of the event DNA. The amplicon is of a length and has a sequence that is also diagnostic for the event. The amplicon may range in length from the combined length of the primer pairs plus one nucleotide base pair, or plus about fifty nucleotide base pairs, or plus about two hundred-fifty nucleotide base pairs, or plus about three hundred-fifty nucleotide base pairs or more.

Alternatively, a primer pair may be derived from flanking genomic sequence on both sides of the inserted DNA so as to produce an amplicon that includes the entire insert nucleotide sequence. A member of a primer pair derived from the plant genomic sequence may be located a distance from the inserted transgene DNA molecule, the distance may range from one nucleotide base pair up to about twenty thousand nucleotide base pairs. As used herein, "amplicon" refers to the product of a DNA thermal amplification reaction.

Nucleic acid amplification may be accomplished by any of the various nucleic acid amplification reaction methods known in the art, including the polymerase chain reaction (PCR). A variety of amplification methods are known in the art and are described, inter alia, in U.S. Pat. Nos. 4,683,195 and 4,683,202 and in Innis et al. (1990). PCR amplification methods have been developed to amplify up to 22 kb of genomic DNA and up to 42 kb of bacteriophage DNA (Cheng et al., 1994). These methods as well as other methods known in PCR amplification may be used in the practice of the present invention. The sequence of the heterologous DNA insert or flanking sequence from soybean event SHZD32-01 may be verified, and corrected by amplifying such molecules from the event genome using primers derived from the sequences provided herein followed by standard DNA sequencing methods applied to the PCR amplicon or to isolated cloned transgene/genomic DNA.

Figure 1:
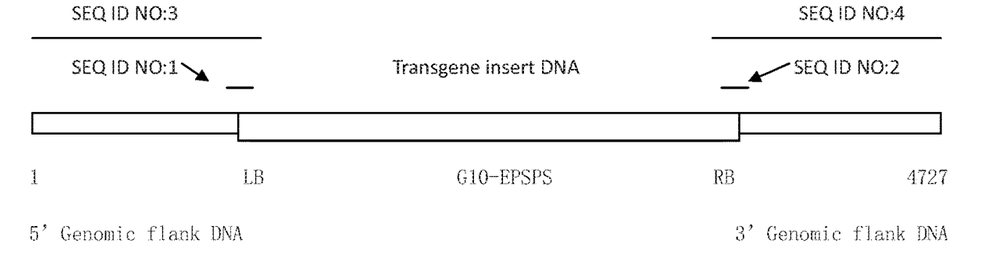
FIG. 1 illustrates the genomic insert of the SHZD32-01 transgene into the soybean genome.

DNA detection kits may be developed using the compositions disclosed herein and the methods described or known in the art of DNA detection. The kits are useful for the identification of soybean event DNA in a sample and may be applied to methods for breeding soybean plants comprising DNA. The kits may comprise DNA primers or probes that are homologous or complementary to SEQ ID NOS: 1-4 and 9 or DNA primers or probes homologous or complementary to DNA contained in the transgene genetic elements of DNA, these DNA sequences may be used as primers in DNA amplification reactions or as probes in a DNA hybridization method. The structure of the DNA of the transgene genetic elements contained in the soybean genome as illustrated in FIG. 1 comprises 5' genomic region of the soybean Zhongdou 32 genome flanking the transgene insert, terminator (without left border sequence of T-DNA), glyphosate resistant gene G10-EPSPS, an *Arabidopsis* chloroplast transit peptide coding sequences, enhancer, promoter, a portion of the right border region (RB) from *Agrobacterium tumefaciens*, and adjacent 3' genomic region of the soybean Zhongdou 32 genome flanking the transgene insert. DNA molecules useful as primers in DNA amplification methods may be derived from the sequences of the genetic elements of the transgene inset contained in the soybean event SHZD32-01. These primer molecules may be used as part of a primer set that also includes a DNA primer molecule derived from the genome of soybean flanking the transgene insert. Soybean event SHZD32-01 is produced by transgenic of soybean line Zhongdou 32 by an *agrobacterium*-mediated method.

The present invention has the following beneficial effects:

In the present invention, foreign herbicide tolerant transgenic gene has been inserted into the genome of *Glycine max*. As a result, a unique DNA molecule is made and partial sequences of the DNA molecule are disclosed. Soybean strains of the present invention comprise the event SHZD32-01 and exhibit strong tolerance to herbicide glyphosate. The glyphosate tolerant soybean transgenic event of the present invention is helpful for weed control. The detection of transgenic event is useful for the identification of soybean event DNA in a sample and may be applied to methods for breeding soybean plants comprising DNA.

The classification of the deposited biological material is soybean cultivated soybean species, soybean SHZD32-01 *Glycine max* (L) Merr. Soybean event SHZD320-01 have representative seeds deposited with China Center for Type Culture Collection (CCTCC) with Accession CCTCC NO: P201513. Address: Wuhan university, Wuhan, China; Date of deposit: Aug. 18, 2015, Number of deposit: CCTCC NO:P201513.

DETAILED DESCRIPTION OF THE INVENTION AND EMBODIMENTS

The following examples are included to explain the present invention but do not limit the scope of the present invention. Without departing the basic spirit and scope of the present invention, those of skill in the art may modify the disclosed examples and still obtain similar results.

EXAMPLE 1

Specific Amplification of DNA from SHZD32-01 Genome

DNA from transgenic soybean event SHZD32-01 is extracted from tissue comprising soybean seeds, vegetative tissue, or meal. The DNA is isolated from the tissue using biotech company's DNA extraction kit according to the manufacturer's instructions. The DNA may also be extracted by CTAB method.

A PCR product is produced that comprises a portion of the genomic DNA flanking the 5' end of the T-DNA insertion in the genome of a plant comprising SHZD32-01. The DNA product comprises SEQ ID NO:3. The PCR may be performed using one primer designed to hybridize to the genomic DNA sequences flanking the 5' end of the transgene insert (DNA primer A, SEQ ID NO:5; see FIG. 1) paired with a second primer (DNA primer B, SEQ ID NO:6) located in the transgene terminator region (seen in SEQ ID NO:9).

A PCR product is produced from the 3' end of the transgene insert that comprises a portion of the genomic DNA flanking the 3' end of the T-DNA insertion in the genome of a plant comprising SHZD32-01. This DNA product comprises SEQ ID NO:4.

PCR may be performed using one primer designed to hybridize to the genomic DNA sequences flanking the 3' end of the insert of each event (DNA primer D, SEQ ID NO:8) and paired with a second primer (DNA primer C, SEQ ID NO:7) located in the region between the promoter and the vector.

DNA event primer pairs are used to produce an amplicon diagnostic for SHZD32-01 genomic DNA. These event primer pairs include, but are not limited to primers A and B (SEQ ID NO: 5 and 6) and event primer pairs C and D (SEQ ID NO: 7 and 8), that are used in the described DNA amplification method. In addition to these primer pairs, any primer pair derived from SEQ ID NO:3 or SEQ ID NO:4, or the complements thereof, that when used in a DNA amplification reaction produces an amplicon that comprises SEQ ID NO: 1 or SEQ ID NO:2 diagnostic for soybean SHZD32-01 event-derived tissue, respectively, may be utilized.

Any modification of the methods used to produce a diagnostic amplicon for SHZD32-01 is within the ordinary skill of the art. An extract putatively comprising a DNA of a soybean plant or seed comprising SHZD32-01, or a product derived from a plant comprising SHZD32-01 that, when tested in a DNA amplification method, produces a diagnostic amplicon for soybean event SHZD32-01 may be utilized as a template for amplification to determine whether SHZD32-01 is present.

The amplicon is produced by the use of at least one primer sequence derived from SEQ ID NO:3 or SEQ ID NO:4 that when used in a PCR method produces a diagnostic amplicon for the event SHZD32-01. Amplification reactions are performed using PCR instrument (ABI, 2720) by following steps:

DNA Extraction:

Grind fresh leaves from soybean plant in liquid nitrogen. Plus 500 μl 2XCTAB extract buffer, soak powders of soybean plant and mix plant powder with CTAB well, keep it in 60° C. for 30-60 min, reverse tube every 10 minutes. Cool down centrifuge tubes to room temperature, add 500 μl pre-cold Chloroform-isoamylalcohol (4° C.) (24:1 v/v), slightly reverse, standing 10 min. Centrifuge 10 min at 12000 r/min under 4° C. Take supernatant to a new tube, add equal volume pre-cold isopropanol (−20° C.), mix well and stay in refrigerator for 30 minutes. Centrifuge 10 min at 12000 r/min under 4° C. Discard supernatant, reverse tubes on filter paper, wash with 70% ethanol twice, air-dry in hood. Dissolve DNA in 50 μl TE buffer, add 1 μl RNaseA (10 mg/ml), incubate 15 minutes at 37° C., store in −20° C. Examine DNA concentration with Spectrophotometer ND-1000, loading 1.5 μl each time. Examine DNA concentration with agarose gel electrophoresis: make 0.8% agarose with some EB. Electrophoresis under voltage 120V, current 140 mA.

Reagents Needed to be Prepared:

CTAB extracting solution: 2% CTAB, 1.4 mol/L NaCl, 100 mmol/L Tris-HCl, pH8.0, 20 mmol/L EDTA, and pH8.0.

CTAB precipitation solution: 1% CTAB, 50 mmol/L Tris-HCl, pH 8.0, 10 mmol/L EDTA, and pH8.0.

TE buffer solution: 10 mmol/L Tris-HCl and 1 mmol/L EDTA (pH 8.0).

PCR detection: the PCR reactions are performed under the following conditions: 35 cycles denatured at 94° C. for 3 min, denatured at 94° C. for 30 s, annealed at 55° C. for 30 s, extended at 72° C. for 1 min. A 725 bp sequence amplicon is obtained.

After the cycle, the product is extended at 72° C. for 10 min and then stored at 4° C. Take 10 μl PCR product, examine with 1.2% agarose gel electrophoresis for 40 min, observe and take pictures under UV light.

The DNA is transferred to Hybond-N membrane (Amersham Pharmacia Biotech, Buckingamshire, England) using a Turbo blotter (Schleicher and Schuell, Das-sel, Germany) for 4-6 hours and then fixed to the membrane using a UV light.

EXAMPLE 2

Sequence Determination of Transgene/Genomic Region and Southern Analysis

DNA sequencing of the PCR products provides for DNA that may be used to design additional DNA molecules as primers and probes for the identification of soybean plants or seed comprising SHZD32-01. PCR products of the expected sizes representing the 5' and 3' transgene/genomic sequences are isolated by separation of the PCR products on a 2.0% agarose gel by electrophoresis. PCR products are isolated that include the 5' and 3' DNA regions that span the insert junction between the transgene insertion into the soybean genome. The 5' and 3' PCR products for SHZD32-01 are purified by agarose gel electrophoresis followed by isolation from the agarose matrix using the SK8131 DNA Gel Extraction Kit. The DNA fragments are ligated with pMD18-T and then sequenced through sequencing company.

A DNA sequence is determined for the nucleic acid representing the transgene/genomic region of event SHZD32-01 as illustrated in FIG. 1 and identified as SEQ ID NO:9. The genomic and transgene elements that are contained in SEQ ID NO:9 are described in Table 1. The 5' and 3' flanking regions are included in SEQ ID NO:9 and given in SEQ ID NOS:21 and 22.

The junction sequences are relatively short nucleotide molecules that are novel nucleic acid molecules and are diagnostic for SHZD32-01 DNA when detected in a polynucleic acid detection assay. The junction sequences in SEQ ID NO: 1 and SEQ ID NO:2 represent 10 polynucleotides on each side of an insertion site of the transgene fragment and soybean genomic DNA in SHZD32-01. Longer or shorter polynucleotide junction sequences may be selected from SEQ ID NO:3 or SEQ ID NO:4. The junction molecules (5' junction region SEQ ID NO:1, and 3' junction region SEQ ID NO:2) are useful as DNA probes or as DNA primer molecules in methods for DNA detection. Primers and probes used in for detection of an event specific DNA molecule are developed for event SHZD32-01. The primer molecules are referred to as SEQ ID NO:10, SEQ ID NO:11, SEQ ID NO:14, SEQ ID NO:15, SEQ ID NO: 16, SEQ ID NO:17 and the probe molecules are referred to as SEQ ID NO: 12, SEQ ID NO: 13, SEQ ID NO: 10, and SEQ ID NO:11. Additional primers used to produce an amplicon from soyfoods include SEQ ID NOS: 18-20.

TABLE 1

Genome and genetic element annotation of the transgene/genomic DNA fragment (SEQ ID NO: 9) contained in the genome of soybean comprising SHZD32-01.

| Location of genetic element | Sequence | Function |
|---|---|---|
| Sequence flanking 5' end of the insert | 1-834 | SOYBEAN GENOMIC DNA |
| 5' junction region | 824-844 | DNA region spanning the transgene insertion |
| CaMVpolyA terminator | 841-1024 | CaMV 35S terminator of the Cauliflower mosaic virus |
| G10-EPSPS | 1030-2379 | Coding sequence of 5-enolpyruvyl-3-phosphoshikimate synthase from *Deinococcus radiodurans* R1 |
| Signaling peptide | 2586-2380 | Sequencing coding chloroplast transit peptide from *Arabidopsis thaliana* |
| enhancer | 2742-2587 | Enhancer sequence from tobacco mosaic virus |
| promoter | 3493-2724 | CaMV 35S promoter of the Cauliflower mosaic virus |
| LacZ alpha | 3986-3752 | Sequence points used in multi-DNA cloning |
| 3' junction region | 3994-4014 | DNA region spanning the transgenic insertion of soybean genome |
| 3' junction region Sequence flanking 3' end of the insert | 4005-4727 | Soybean genomic DNA |

Southern Blot Analysis

Genomic DNA from a plant comprising SHZD32-01 and control soybean genomic DNA (~15 μg of each) is digested with various restriction enzymes (140U) in a total volume of 150 μl including 15 μl of the corresponding manufacturer's buffer (NEB, Beverly, Mass.). Restriction endonucleases, e.g., BamH I, Pst I, HindIII, and Xba I, are used in the Southern analysis of SHZD32-01. Endonuclease digests are performed at the appropriate temperature for at least 6 hours. After incubating, the DNA is precipitated with 3M sodium acetate and 2.5 volumes of ethanol. Subsequently, the DNA is washed with 70% ethanol, dried, and resuspended in 40 μl of TBE. Loading buffer (0.2×) is added to the samples and then subjected to electrophoresis on agarose gels (0.8%) for 16-18 hours at 30 volts. The gels are stained with ethidium-bromide, then treated with a depurination solution (0.125N HCL) for 10 minutes, with a denaturing solution (0.5M sodium hydroxide, 1.5M sodium chloride) for 30 minutes, and finally with a neutralizing solution (0.5M Trizma base, 1.5M sodium chloride) for 30 minutes. The DNA is transferred to Hybond-N membrane (Amersham Pharmacia Biotech, Buckinghamshire, England) using a Turbo blotter (Schleicher and Schuell, Das-sel, Germany) for 4-6 hours and then fixed to the membrane using a UV light.

Membranes are prehybridized with 20 mls of DIG Easy Hyb solution for 2-4 hours at 45° C. Radioactive DNA probes homologous or complementary to SEQ ID NO: 1, or SEQ ID NO:2, or SEQ ID NO:3, or SEQ ID NO:4, or a portion thereof are made using a DNA Labeling kit. Unincorporated nucleotides are removed. The prehybridization solution is replaced with 10 mls of pre-warmed DIG Easy Hyb solution comprising the denatured probe. The blots are hybridized at 45° C. for 16-18 hours.

Blots are washed with a low stringency solution (5×SSC, 0.1×SDS) at 45° C. and then repeatedly washed with a higher stringency solution (0.1×SSC, 0.1% SDS) at 65° C. The blots are exposed. These methods and conditions exemplified may be modified by those skilled in the art of detecting DNA in a sample.

EXAMPLE 3

Weed Control

Controlling the growth of weeds in a field of soybeans comprising SHZD32-01. A field is planted with soybean seeds comprising SHZD32-01, the seeds are allowed to germinate into plants and the field of plants is treated with a herbicide formulation comprising glyphosate. An effective dose of a glyphosate formulation at treatment rates of from about 0.25 lb ae/A (pounds of glyphosate acid equivalent/acre) to 3 or more lb ae/A is applied to the field. Rates often applied range from about 0.75 lb ae/A to 1.5 lb ae/A at a frequency of one or more treatments during the growing season as necessary to control the growth of weeds in a field. Seeds from the plants comprising SHZD32-01 are harvested from the treated plants.

Soybean event SHZD320-01 as disclosed above and set forth in the claims have representative seeds deposited with China Center for Type Culture Collection (CCTCC) with Accession CCTCC NO: P201513. Address: Wuhan university, Wuhan, China; Postal code: 430072; the classification of the deposited biological material is soybean cultivated soybean species, soybean SHZD32-01 *Glycine max* (L) Merr; Number of deposit: CCTCC NO:P201513; Date of deposit: Aug. 18, 2015, the retention period is 30 years (calculated from the date of receipt by the deposit center), retained for another five years if the request to provide a culture sample is received before expiration.

Based on the principles of the present invention as provided above, persons skilled in the art may modify the arrangement of the procedures and details without departing from such principles of the present invention. Our claims cover all modifications that are within the spirit and scope of the claims of the present invention.

We claim:

1. A soybean plant or part thereof, comprising
a soybean event SHZD32-01, wherein representative soybean seeds are deposited at China Center for Type Culture Collection (CCTCC), having an Accession No. P201513, an address at Wuhan university, Luojiashan, Wuchang, Wuhan, 430072, China; date of deposit is Aug. 18, 2015; and deposited biological material is described as soybean cultivated soybean species, soybean SHZD32-01 *Glycine max* (L) Merr.

2. A seed of the soybean plant of claim 1, wherein the seed comprises the soybean event SHZD32-01.

3. A progeny soybean plant of the soybean plant of claim 1, wherein the progeny soybean plant is the progeny plant of any generation of the soybean plant and, comprises the soybean event SHZD32-01.

4. The soybean plant part of claim 1, wherein the plant part is a cell, pollen, ovule, flower, shoot, root, or leaf.

5. The soybean plant or part thereof as described in claim 1, wherein the soybean plant or part thereof is capable of producing a diagnostic amplicon, and the diagnostic amplicon comprises SEQ ID NO: 1 or SEQ ID NO: 2.

6. The seed of the soybean plant of claim 2, wherein the seed is capable of producing a diagnostic amplicon, and the diagnostic amplicon comprises SEQ ID NO: 1 or SEQ ID NO: 2.

7. A soybean commodity product produced from the seed of the soybean plant of claim 2, wherein the commodity product is flake, flour, meal, or oil, and
wherein the commodity product comprises a nucleic acid that produces a diagnostic amplicon for event SHZD32-01, and the diagnostic amplicon comprises SEQ ID NO: 1 or SEQ ID NO: 2 when tested by a DNA amplification method.

8. A method for producing a glyphosate tolerant soybean plant, comprising
introducing an event SHZD32-01 having representative seeds deposited at China Center for Type Culture Collection (CCTCC), having an Accession No. P201513, an address at Wuhan university, Luojiashan, Wuchang, Wuhan, 430072, China; date of deposit is Aug. 18, 2015; and deposited biological material is described as soybean cultivated soybean species, soybean SHZD32-01 *Glycine max* (L) Merr., into a genome of a soybean plant by
(a) crossing a first soybean plant comprising the event SHZD32-01 with a second soybean plant lacking the event SHZD32-01 to produce progeny plants; and
(b) selecting at least a first progeny plant that comprises the soybean transgenic event SHZD32-01 and is tolerant to glyphosate.

9. The method of claim 8, further comprising
selfing the progeny plant of the first soybean plant comprising the soybean transgenic event SHZD32-01 and is tolerant to glyphosate to produce a second generation progeny plants, and
selecting at least one homozygous progeny of the first soybean plant comprising the soybean transgenic event SHZD32-01.

10. A glyphosate tolerant soybean plant or part thereof according to claim 8, comprising a glyphosate resistant protein G10-EPSPS, and the glyphosate tolerant soybean plant or part thereof is capable of producing a diagnostic amplicon for the soybean transgenic event SHZD32-01;
and the diagnostic amplicon for the soybean transgenic event SHZD32-01 comprises SEQ ID NO: 1 or SEQ ID NO: 2.

11. A method for producing a soybean commodity product according to claim 1, comprising,
(a) obtaining the soybean plant or part thereof of claim 1; and
(b) producing a soybean commodity product from the soybean plant or part thereof, wherein the commodity product is a meal, flour, flakes, protein isolate, or oil.

12. A method for controlling the growth of weeds in a field planted with soybean plants according to claim 1, comprising
treating the field with an amount of glyphosate effective to control the growth of weeds, and the soybean plants exhibiting tolerance to the glyphosate,
wherein treating the field is carried out at Stage V1 to R4 during the growth of the soybean.

13. A recombinant DNA molecule of a soybean event SHZD32-01, comprising a nucleotide sequence selected from the group consisting of SEQ ID NO: 1, SEQ ID NO: 2, SEQ ID NO: 3, SEQ ID NO: 4, SEQ ID NO: 9, and the complete complementary sequences thereof, wherein the recombinant DNA molecule is from the soybean event SHZD32-01, and a representative soybean seed comprising the soybean event SHZD32-01 is deposited at China Center for Type Culture Collection under CCTCC accession number P201513.

14. The recombinant DNA molecule of claim 13, wherein the recombinant molecule is present in soybean plants, soybean plant cells, soybean seeds, soybean plant parts, or in commercial products.

15. A DNA primer or probe of the recombinant DNA molecule of claim 13, wherein the DNA primer or probe comprises a continuous nucleic acid sequence that is long enough to include SEQ ID NO: 9 or its complementary sequence, and is used for diagnosing the soybean event SHZD32-01 and hybridizes with a DNA molecule having a nucleic acid sequence that is SEQ ID NO: 1 to 4 and 9 under high hybridization conditions, and does not hybridize with a DNA molecule that does not have the nucleic acid sequence that is SEQ ID NO: 1 to 4 and 9 under high hybridization conditions, wherein the high hybridization conditions are being repeatedly washed with a high stringency solution.

16. A pair of DNA molecules according to claim 13, wherein the pair of DNA molecules are a first DNA molecule and a second DNA molecule that is different from the first DNA molecule, the first and the second DNA molecules each has a continuous nucleic acid sequence that is from SEQ ID NO: 9 or its complete complementary sequence and used as DNA primers with the recombinant DNA molecule of the soybean event SHZD32-01 for an amplification reaction to produce a diagnostic amplicon in a diagnostic sample, the diagnostic amplicon being from the soybean event SHZD32-01 and comprising SEQ ID NO: 1 or SEQ ID NO: 2.

17. A method for detecting the recombinant DNA molecule of the soybean event SHZD32-01 according to claim 15 in a sample, comprising
   (a) contacting a DNA from a sample with the DNA primer or probe of claim 15,
   (b) hybridizing the DNA from the sample and the DNA primer or probe under high hybridization conditions, wherein the high hybridization conditions are being repeatedly washed with a high stringency solution, and
   (c) detecting hybridization of the DNA from the sample and the DNA primer or probe, wherein the recombinant DNA molecule of the soybean event SHZD32-01 is present in the sample, if the DNA primer or probe hybridizes with the DNA molecule from the sample.

18. A method for detecting the recombinant DNA molecule of the soybean event SHZD32-01 in the sample according to claim 16, comprising
   (a) contacting a DNA from a sample with the DNA pair of claim 16,
   (b) conducting an amplification reaction to produce a diagnostic amplicon having a nucleic acid sequence that comprises SEQ ID NO: 1 to 4, SEQ ID NO: 9, or complete complementary sequences thereof, and
   (c) detecting the diagnostic amplicon, wherein the recombinant DNA molecule of the soybean event SHZD32-01 is present in the sample, if the diagnostic amplicon is present from the amplification reaction.

19. A DNA testing kit, comprising a pair of DNA primers or probes as described in claim 15, wherein the DNA primers comprise at least one DNA molecule that comprises a continuous nucleic acid sequence that is long enough to include a sequence of SEQ ID NO: 9 or its complementary sequence, and the pair of DNA primers are used for diagnosing the soybean event SHZD32-01, and (b) at least one DNA probe is for diagnosing the soybean event SHZD32-01.

20. A method of transforming a plant with the recombinant DNA molecule as described in claim 13, comprising
   inserting the recombinant DNA molecule into the genome of a plant,
   wherein the insertion sites have nucleic acid sequences having SEQ ID NO:1 and SEQ ID NO: 2, respectively.

* * * * *